(12) United States Patent
Boström (10) Patent No.: US 10,881,797 B2
(45) Date of Patent: Jan. 5, 2021

(54) DRIVE MECHANISM FOR AN AUTOINJECTOR

(71) Applicant: Carebay Europe Ltd., Sliema (MT)

(72) Inventor: Anders Boström, Solna (SE)

(73) Assignee: SHL MEDICAL AG, Zug (CH)

( * ) Notice: Subject to any disclaimer, the term of this patent is extended or adjusted under 35 U.S.C. 154(b) by 352 days.

(21) Appl. No.: 15/568,816

(22) PCT Filed: Apr. 4, 2016

(86) PCT No.: PCT/EP2016/057342
§ 371 (c)(1),
(2) Date: Oct. 24, 2017

(87) PCT Pub. No.: WO2016/169756
PCT Pub. Date: Oct. 27, 2016

(65) Prior Publication Data
US 2018/0104415 A1    Apr. 19, 2018

(30) Foreign Application Priority Data

Apr. 24, 2015 (SE) ........................ 1550496

(51) Int. Cl.
*A61M 5/20* (2006.01)
*A61M 5/315* (2006.01)
*A61M 5/32* (2006.01)

(52) U.S. Cl.
CPC ...... *A61M 5/2033* (2013.01); *A61M 5/31511* (2013.01); *A61M 5/31565* (2013.01); *A61M 5/326* (2013.01); *A61M 2005/2013* (2013.01)

(58) Field of Classification Search
CPC .. A61M 5/20; A61M 5/2033; A61M 5/31565; A61M 5/31576; A61M 5/31578;
(Continued)

(56) References Cited

U.S. PATENT DOCUMENTS

2008/0300550 A1* 12/2008 Schiller .............. A61M 5/31511
604/220
2012/0265136 A1* 10/2012 Lawlis ................... A61K 38/24
604/110

(Continued)

FOREIGN PATENT DOCUMENTS

WO    2011123024 A1    6/2011
WO    2013016832 A1    2/2013

*Primary Examiner* — Kami A Bosworth
(74) *Attorney, Agent, or Firm* — McDonnell Boehnen Hulbert & Berghoff LLP (57) ABSTRACT

The present invention relates to a drive mechanism for use with a medicament delivery device, comprising a plunger rod (68), a drive spring (72) operably arranged to the plunger rod, an actuator (52) comprising a holding member (60) releasably engaged to the plunger rod (68) for holding said plunger rod (68) with said drive spring (72) in a tensioned state, a rotator (38) operably connected and movable relative to said actuator (52) and configured to interact with said holding member for holding said holding member in engagement with the plunger rod, an activator (30) operably connected to said rotator (38). The invention is characterized in that the activator (30) is configured to rotate and subsequently linearly displace the rotator (38) in relation to the actuator (52) such that said holding member (60) is released from the plunger rod (68).

17 Claims, 7 Drawing Sheets

(58) Field of Classification Search
CPC ...... A61M 5/31583; A61M 2005/2013; A61M 2005/208; A61M 5/3148; A61M 5/31511; A61M 5/326; A61M 2005/31588
See application file for complete search history.

(56) References Cited

U.S. PATENT DOCUMENTS

| | | | |
|---|---|---|---|
| 2013/0035642 A1* | 2/2013 | Daniel | A61M 5/2033 604/189 |
| 2013/0324934 A1* | 12/2013 | Holmqvist | A61M 5/2033 604/192 |

* cited by examiner

DRIVE MECHANISM FOR AN AUTOINJECTOR

CROSS REFERENCE TO RELATED APPLICATIONS

The present application is a U.S. National Phase Application pursuant to 35 U.S.C. § 371 of International Application No. PCT/EP2016/057342 filed Apr. 4, 2016, which claims priority to Swedish Patent Application No. 1550496-2 filed Apr. 24, 2015. The entire disclosure contents of these applications are hereby incorporated by reference into the present application.

The present invention relates to a drive mechanism for medicament delivery devices and in particular medicament delivery devices provided with a high degree of automated functions.

BACKGROUND OF INVENTION

There is a constant development of medicament delivery devices that are intended and designed to be used and handled by users that are not qualified nursing staff or physicians, i.e. handled by the patients themselves. The applicant of the present invention has developed a large number of medicament delivery devices that display a high degree of automated functions comprising mixing of drug, priming, penetration, injection withdrawal and/or extension of medicament delivery member guard.

In order to create a number of these functions while keeping the number of components as low as possible, a so called rotator has often been utilized, which is a generally tubular element that is capable of rotating inside the housing of a medicament delivery device, where the rotation triggers, enables and/or performs different functions.

Document WO2011/123024 discloses a medicament delivery device arranged with such a rotator. The rotator is operated by a medicament delivery member guard during penetration sequence. The rotator in turn affects holding elements that holds a plunger rod in a tensioned state. The holding elements are in the form of arms provided with inwardly directed protrusions fitting into recesses of the plunger rod.

When the rotator has turned a certain rotational angle, wherein the penetration sequence is completed, the holding members are released from the rotator, whereby the plunger rod also is freed and is moved in the proximal direction for delivering a dose of medicament. The rotator also has additional features such as locking of the medicament delivery member guard in an extended position after removal of the medicament delivery device after injection.

Even though the rotator solution works very well in most instances and provides a reduced number of components as compared to more conventional solutions, there have been occurrences when the rotational movement of the rotator has caused a bending of the holding members due to the friction between the rotator and the holding members. This in turn has led to a jamming of the holding members such that the plunger rod has not been released as it should.

BRIEF DESCRIPTION OF INVENTION

The aim of the present invention is to remedy the drawbacks of the state of the art drive mechanisms. This aim is obtained by a drive mechanism for a medicament delivery device having the features of the independent patent claims. Preferable embodiments are found in the dependent patent claims.

The present invention relates to a drive mechanism for use with a medicament delivery device. The drive mechanism preferably comprises a plunger rod and a drive spring operably arranged to plunger rod wherein the plunger rod is arranged to act on a stopper arranged in a medicament container.

The drive mechanism may further be arranged with an actuator comprising a holding member releasably engaged to the plunger rod for holding said plunger rod with said drive spring in a tensioned state. Also a rotator is operably connected and movable relative to said actuator and configured to interact with said holding member for holding said holding member in engagement with the plunger rod.

Further, an activator may be operably connected to the rotator, in that the activator is configured to rotate and subsequently linearly displace the rotator in relation to the actuator such that holding member is released from the plunger rod. With this solution it is possible to avoid the previous problems associated with the rotation of the rotator prior to unlocking of the actuator, because the final movement is a linear movement. The risk of jamming of the holding members is then avoided or at least substantially reduced.

In order to control the movement of the rotator, the actuator may be arranged with a guide surface on which the rotator rests when rotated from a first position to a second position. In order to further control the movement of the rotator, it may be arranged with a cut-out, in which the guide surface can enter in the second position for allowing a linear move of the rotator. Thus, in the rotational movement between the first and the second position, the rotator is guided by the guide surface, preventing any linear movement, and then in the second position, the linear movement is provided in that the guide surface enters the cut-out.

In order to provide a rotational movement, the rotator may comprise first guide ridges that are inclined in relation to a longitudinal direction, on which first guide ridges the activator acts for rotating said rotator. Thus the inclined surface provides the means for rotating the rotator from the first position to the second position.

The rotator may further comprise second guide ridges interconnected to the first guide ridges, wherein the second guide ridges are generally transversal in relation to the longitudinal direction, on which second guide ridges the activator may act for moving said rotator.

In order to obtain the right relative initial positions between the rotator and the actuator, the rotator may comprise first orientating elements operably arranged to interact with second orientating elements on the actuator for providing orientation aid when the rotator is assembled with the actuator.

According to one feasible solution, the first orientating elements may comprise longitudinal grooves and wherein the second orientating elements comprise protrusions arranged to fit into the longitudinal grooves. This enables a proper orientation when the rotator is pushed onto the actuator during assembly of the drive mechanism, reducing the risk of rotational misalignment of the rotator in relation to the actuator.

In order to further provide aid when assembling the drive mechanism, it may further comprise a stop recess on the rotator, in which stop recess the protrusion would fit when the rotator is attached to the actuator. This gives a clear indication that the rotator has been pushed onto the actuator properly. This may also be used as a stop member in the opposite direction, i.e. preventing pulling off of the rotator from the actuator.

According to one feasible solution, the activator may comprise a medicament delivery member guard. Since the medicament delivery member guard is arranged at the proximal end of a medicament delivery device, it may move distally when the medicament delivery device is pressed against a dose delivery site, which movement may be used for rotating and moving the rotator.

These and other aspects of, and advantages with, the present invention will become apparent from the following detailed description of the invention and from the accompanying drawings.

BRIEF DESCRIPTION OF DRAWINGS

In the following detailed description of the invention, reference will be made to the accompanying drawings, of which

DETAILED DESCRIPTION OF THE INVENTION

In the following description, the wording medicament delivery device will be used. In this context, medicament delivery devices may include a number of devices capable of delivering certain doses of medicament to a user, such as e.g. injection devices with or without injection needles, inhalers of all kinds, such as powder, aerosol driven, gas, nebulizers having mouth or nasal pieces, dispensers for medicament in tablet form, eye dispensers, creme/gel dispensers, etc. The medicament delivery devices may be of either disposable type or re-usable type and may be provided with medicament containers suitably arranged for specific drugs in specific forms.

Further, the term "distal part/end" refers to the part/end of the device, or the parts/ends of the members thereof, which under use of the device, is located the furthest away from a delivery site of a patient. Correspondingly, the term "proximal part/end" refers to the part/end of the device, or the parts/ends of the members thereof, which under use of the device is located closest to the delivery site of the patient.

Figure 1:
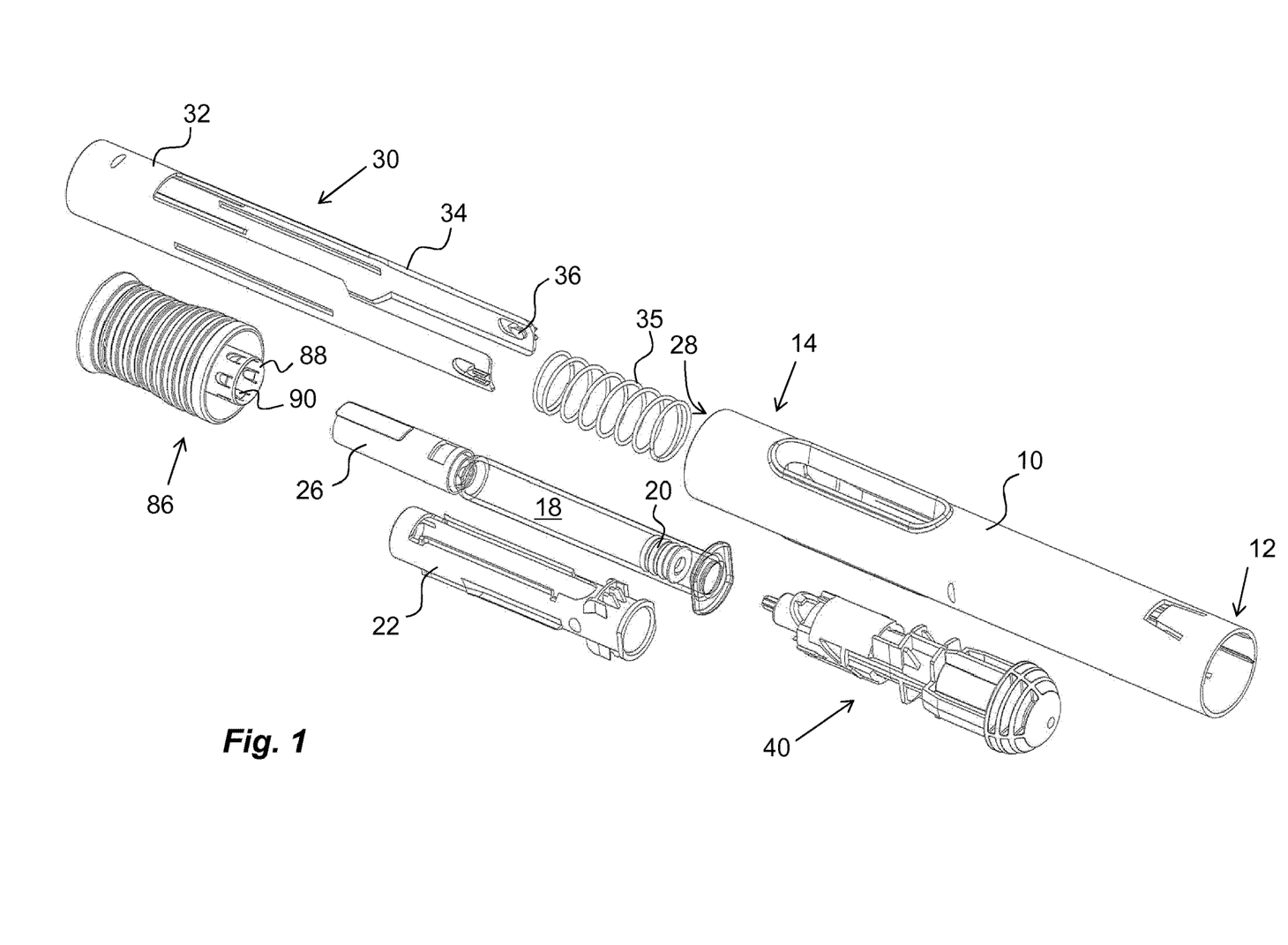
FIG. 1 is an exploded view of one embodiment of a medicament delivery device, FIGS. 2a, b are cross-sectional side views of the device of FIG. 1, FIGS. 3 to 5 are detailed views of components comprised in the device of FIG. 1, and FIGS. 6 to 10 are detailed views of the device of FIG. 1 in different functional states.
Figure 2A:
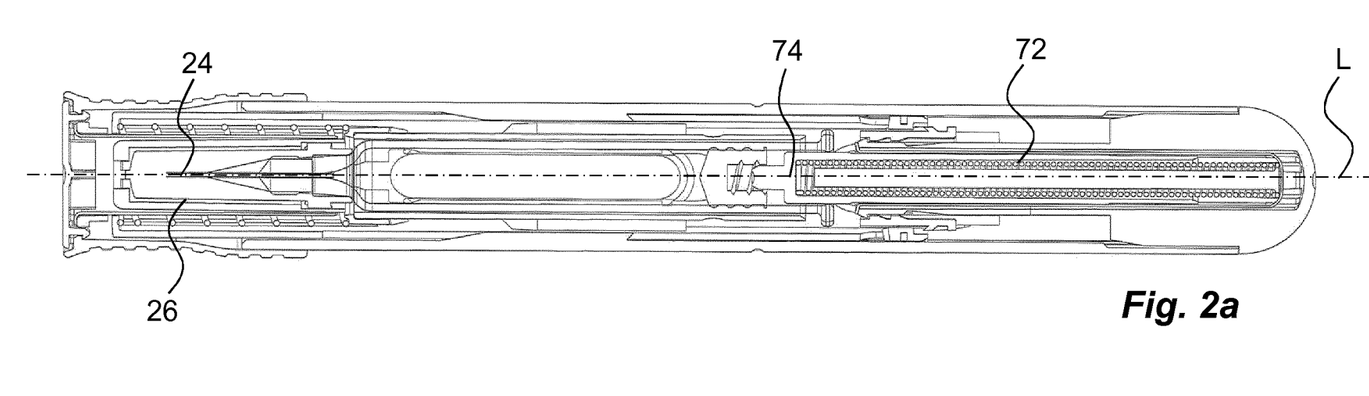
Figure 2B:
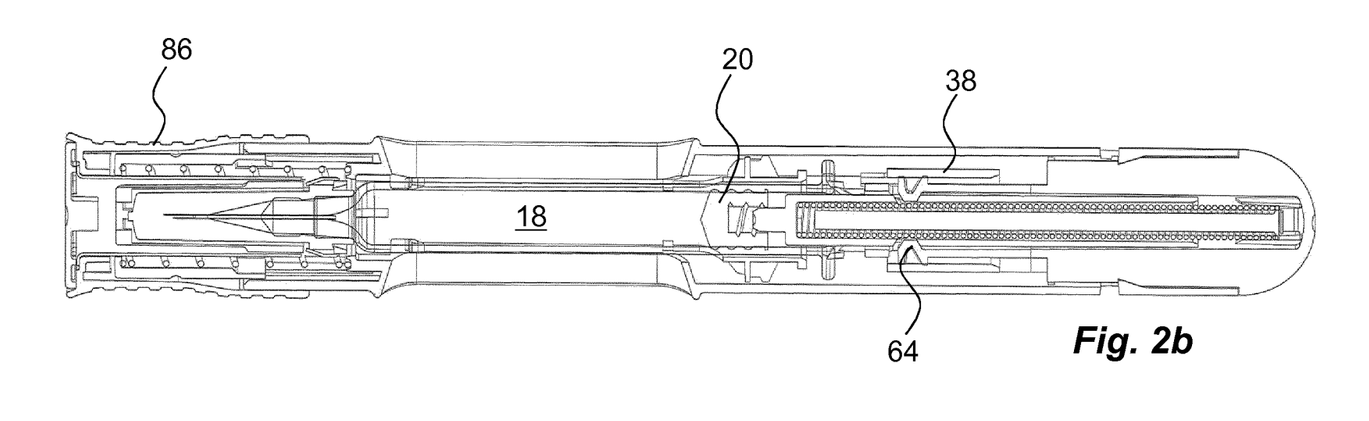

The medicament delivery device shown in the drawings comprises a generally tubular elongated housing 10 having a distal end 12 and a proximal end 14, FIG. 1. The housing 10 is further arranged with windows or openings 16, through which a medicament container 18 can be viewed. The medicament container 18 is arranged with a movable stopper 20. The device further comprises a medicament container holder 22 having a generally tubular shape, FIG. 1. The medicament container holder 22 is arranged to accommodate the medicament container 18, where the medicament container 18 has a proximal end on which a medicament delivery member 24, FIG. 2, is arranged, either made integral or connectable to the medicament container 18. The medicament delivery member 24 is preferably protected before use by a medicament delivery member shield 26 that in the embodiment shown is a so called rigid needle shield or RNS. It is however to be understood that other types of medicament delivery member shields may be used in order to obtain the desired protection of the medicament delivery member 24.

The proximal end of the housing is arranged with a central passage 28, FIG. 1, through which an activator 30 extends. In the present embodiment the activator 30 is a generally tubular medicament delivery member guard. The medicament delivery member guard 30 is in this embodiment an activation mechanism of a drive mechanism comprised in the medicament delivery device. It is arranged slidable i.e. linearly movable in relation to the housing 10 such that the housing 10 with the medicament container 18 and the medicament delivery member 24 are moved in the proximal direction when the medicament delivery device is pressed against a dose delivery site, thereby exposing the medicament delivery member 24 such that a penetration is performed when the medicament delivery member is an injection needle.

The activator 30 comprises a proximal tubular 32 part and two distally directed arms 34 extending from the tubular part 32. A medicament delivery member guard spring 35 is arranged between a distally directed circumferential wall part of the activator 30 and a proximally directed circumferential surface of the housing. The arms 34 are arranged slidable along the medicament container holder 22. At the distal end of the arms 34, inwardly directed protrusions 36 are arranged. The protrusions 36 are arranged to operably interact with a rotator 38, FIGS. 3 and 4, of a drive mechanism comprised in the medicament delivery device, when the activator 30 is moved in relation to the housing, wherein the rotator 38 is positioned distally of the medicament container 18.

Figures 4, 5:
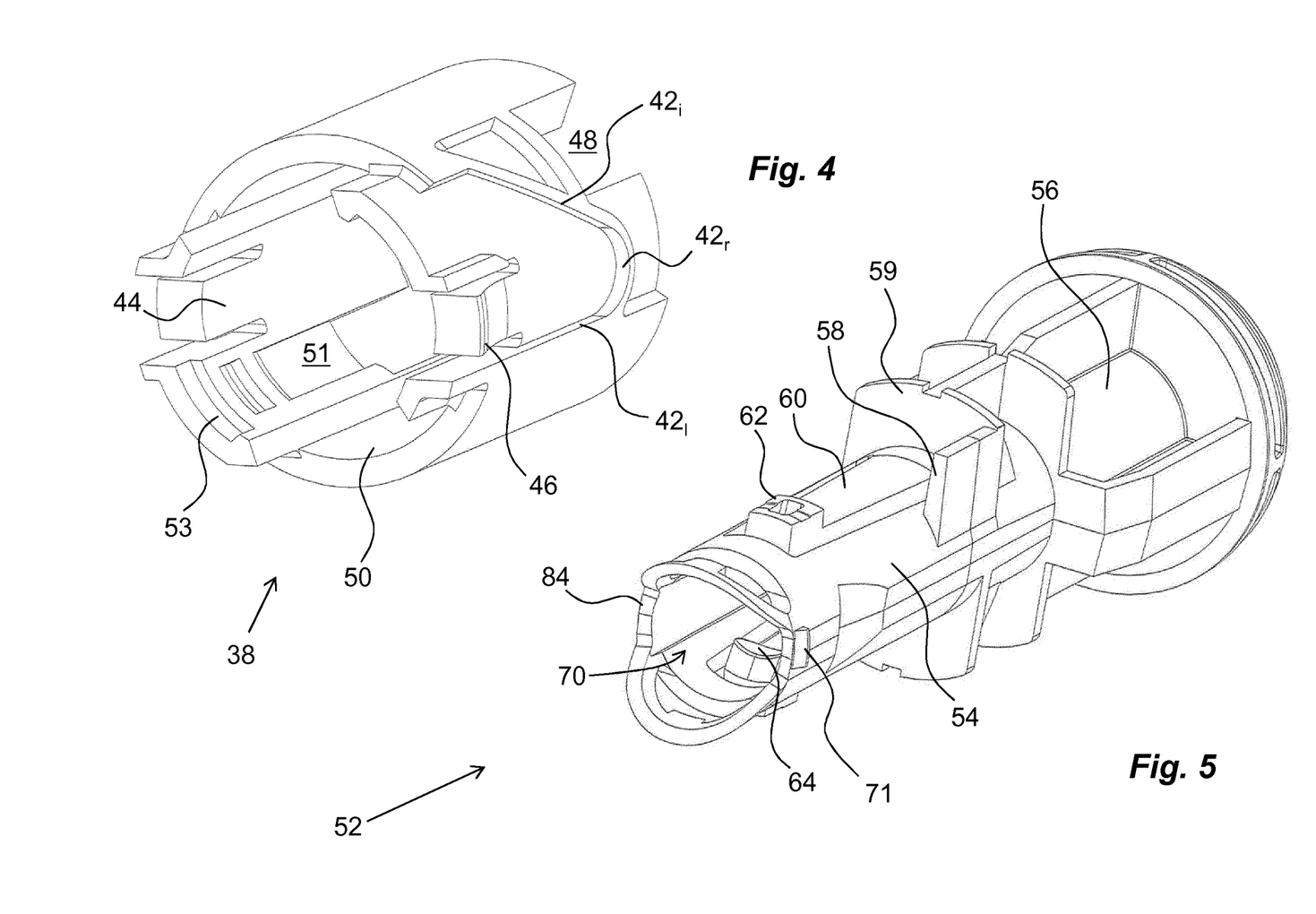

The rotator 38 has a generally tubular shape and is arranged with guide ridges 42, FIG. 4, that are intended to cooperate with the protrusions 36 of the activator 30. The guide ridges comprise a first guide ridge $42_i$ that is inclined in relation to the longitudinal axis L of the device, which inclined first guide ridge interconnects with a rounded second guide ridge $42_r$ as seen in FIG. 4 where the second guide ridge $42_r$ is generally transversal to the longitudinal axis L. A third guide ridge $42_l$ is connected to the second guide ridge, where the third guide ridge $42_l$ is extending in the longitudinal direction. The functions of the guide ridges will be described below. Adjacent the third guide ridge $42_l$ are proximally directed tongues 44, which tongues 44 are arranged with wedge-shaped outwardly directed ledges 46. Further, the rotator is arranged with cut-outs 48 at its distal end surface. Inside the rotator, support surfaces 50 are arranged. Further inside the rotator 38, orientating elements in the form of longitudinal grooves 51 are arranged, from a distal end to almost the proximal end. However, the groove 51 terminates a distance from the proximal end. At the edge of the proximal end in the direction of the longitudinal groove a cut-out 53, forming a stop recess, is made.

Figure 3:
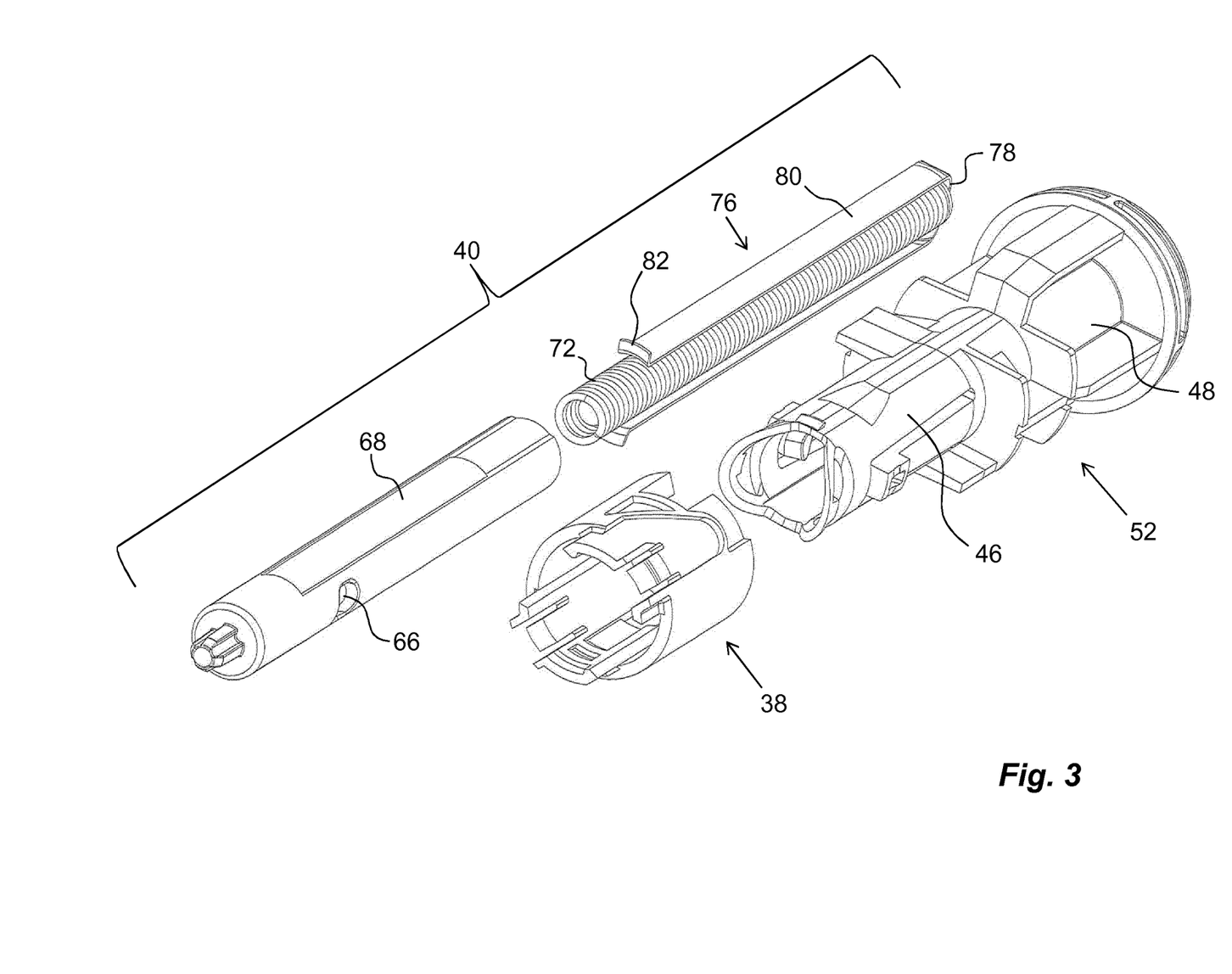

An actuator 52, FIGS. 3 and 5, is in this embodiment a part of the drive mechanism comprised in the medicament delivery device, The actuator 52 is further arranged operably to the rotator 38. It comprises a first proximal tubular section 54 having a diameter slightly smaller than the inner diameter of the rotator 38. It further comprises a second section 56 arranged to fit into and to be attached to a distal part of the housing 10. The second section 56 is provided with proximally directed ledges 58 arranged to interact with the rotator as will be described. The second section is further arranged with proximally directed stop surfaces 59, FIG. 5.

The first section 54 is further arranged with holding members 60 which in the present embodiments are proximally extending arms that are arranged flexible in a generally radial direction. The free ends of the holding members 60 have outwardly extending protrusions 62 that are to interact with the guide surfaces 50 of the rotator 38 as will be described. Further the free ends of the holding members 60 are arranged with inwardly extending protrusions 64, which protrusions 64 are intended to interact with recesses 66 on a generally tubular plunger rod 68, FIG. 3. The generally tubular plunger rod 68 is in this embodiment a part of the drive mechanism comprised in the medicament delivery device. The protrusions 64 extend into a central passage 70 of the actuator 52, in which passage 70 the plunger rod 68 fits. Further, outwardly directed, generally wedge-shaped, protrusions 71 are arranged adjacent the passage 70.

A drive spring 72 which is in this embodiment a part of the drive mechanism comprised in the medicament delivery device, is placed inside a cavity of the hollow plunger rod 68, wherein the drive spring 72 is positioned with a proximal end thereof in contact with an end wall 74 of the plunger rod 68, FIG. 2. The distal end of the drive spring 72 is in contact with a generally U-shaped element, hereafter named activator 76, having a base 78 and two arms 80, FIG. 3. The arms 80 of the activator 76 are directed in the proximal direction along, and in contact with, the outer surface of the plunger rod 68, wherein the free ends of the arms 80 are arranged with generally radially outwardly directed ledges 82. These ledges 82 are arranged to be in contact with a proximally directed surface 84, FIG. 5, surrounding the central passage 70 of the actuator 52.

The medicament delivery device is further arranged with a protective cap 86, FIGS. 1 and 2, having a shape as to be releasably attached to the proximal end of the housing. The protective cap 86 is further arranged with a medicament delivery member shield remover 88 that in the embodiment shown has a generally tubular shape with a diameter so as to extend into the activator and surround the medicament delivery member shield 26. The medicament delivery member shield remover 88 is arranged with grip elements 90 that are inwardly inclined, proximally directed tongues that are capable of gripping into the surface of the medicament delivery member shield when the protective cap is pulled in the proximal direction in relation to the medicament delivery device.

The device is intended to function as follows. When the medicament delivery device is delivered to a user, a medicament container 18 with an attached medicament delivery member shield 26 has been placed in the medicament container holder 22 and a protective cap has been attached to the proximal end of the medicament delivery device. The drive spring 72 has been tensioned in that the plunger rod 68 has been pushed distally relative the actuator 52 such that the inwardly directed protrusions 64 of the holding members 60 of the actuator 52 engage with the recesses 66 of the plunger rod 68, thereby holding the plunger rod 68.

Figures 6, 7:
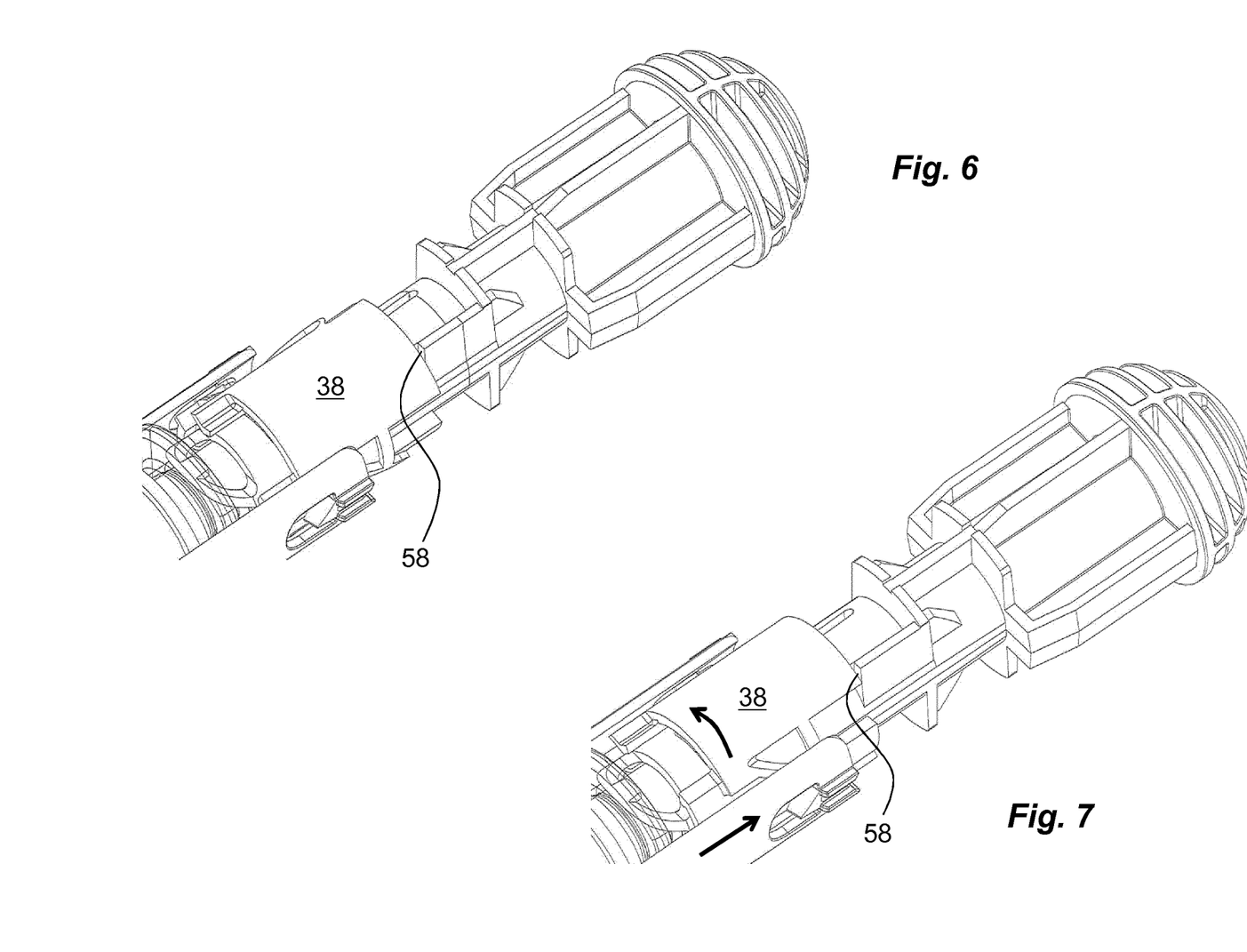

The rotator 38 is then pushed axially onto the actuator 52 from the proximal end. In order have the right rotational orientation of the rotator in relation to the actuator 52, the rotator 38 is held such that the orientating elements, i.e. the protrusions 71, will fit in the longitudinal grooves 51 of the rotator 38. The rotator 38 is then pushed axially until the protrusions 71 fit into the cut-outs 53, which prevents pulling back of the rotator 38. In this rotational position, named first position, the distally directed end of the rotator 38 is in contact with the ledges 58 of the actuator 52 as seen in FIG. 6. The holding members 60 of the actuator 52 are now prevented from moving out of engagement by the support surfaces 50 of the rotator 38 in contact with the outwardly directed protrusions 62 of the holding members 60.

When a dose of medicament is to be delivered, the protective cap 86 is removed from the proximal end of the medicament delivery device by pulling it in the proximal direction. Because of the engagement of the tongues 90 with the medicament delivery member shield 26, the medicament delivery member shield 26 will also be pulled in the proximal direction, removed from the medicament delivery member 24. The proximal end of the medicament delivery device is then pressed against a dose delivery site. This causes the activator 30 to move inside and relative the housing 10. This in turn causes the protrusions 36 of the activator 30 to move along the guide ridges 42 of the rotator 38 such that the protrusions will come in contact with the first guide ridge 42$_i$, which will cause the rotator 38 to turn around the longitudinal axis L of the device i.e. to rotate.

Figures 8, 9:
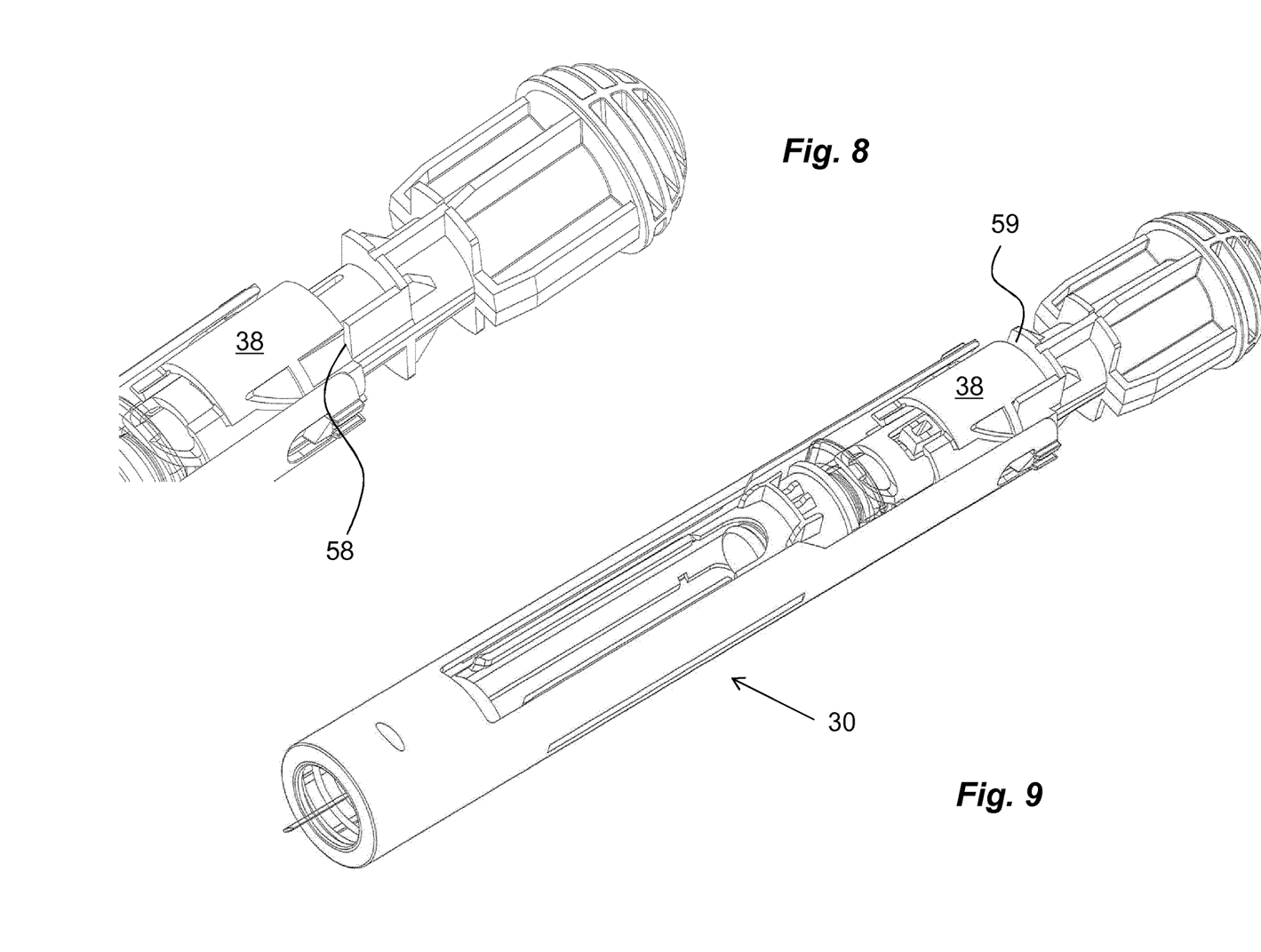
Figure 10:
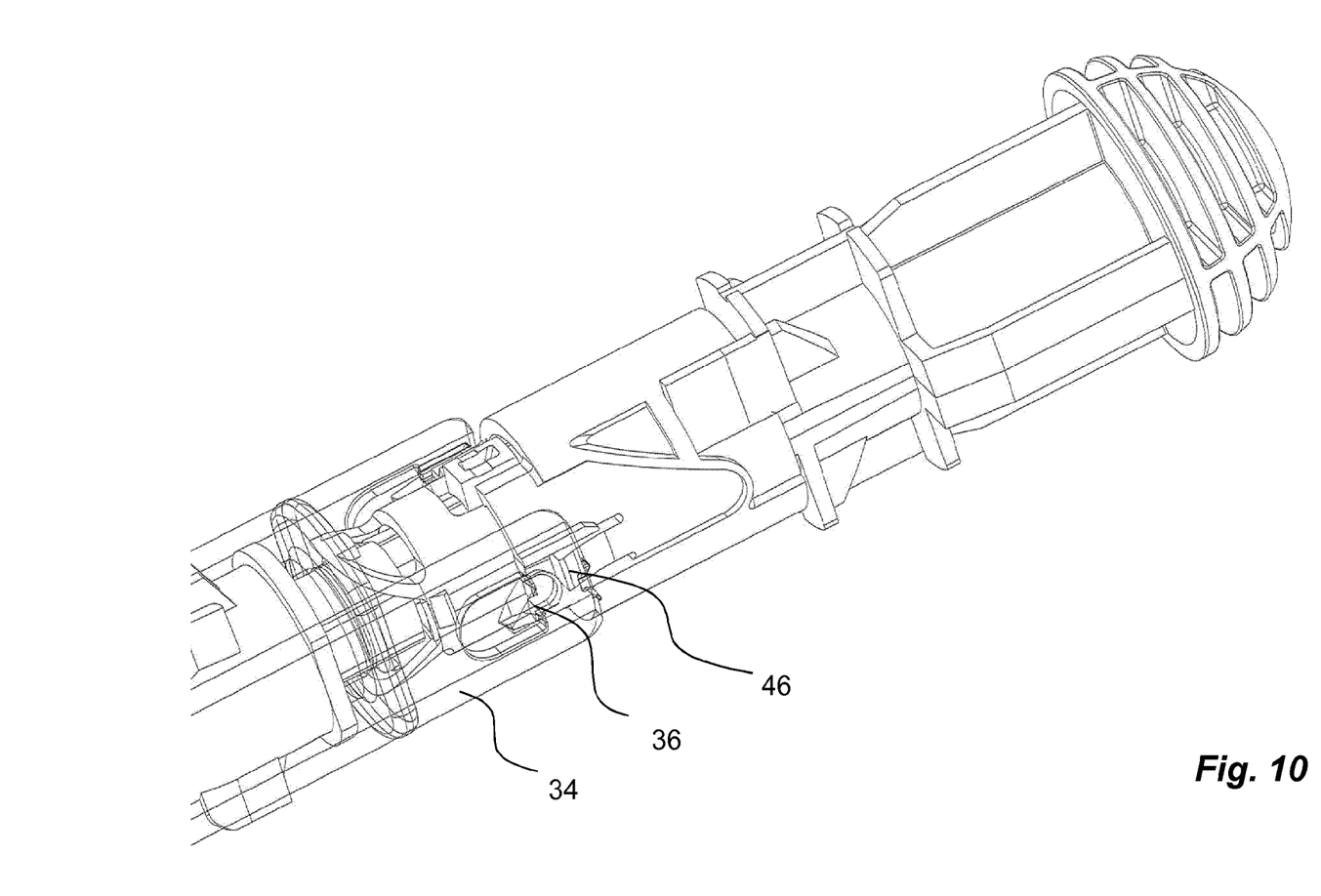

The turning/rotation of the rotator 38 will cause its distally directed end surface to slide along the ledges 58 as seen in FIG. 7 until the protrusions 36 have reached the second guide ridge 42$_r$. At the same time, in this second position, the cut-outs 48 of the rotator 38 have reached the ledges 58, FIG. 8, so that further pushing of the activator 30 will cause the rotator 38 to move axially i.e. to be linearly displaced in the distal direction with its support surfaces sliding in relation to the outwardly directed protrusions of the arms of the actuator. The axial movement of the rotator 38 is stopped when its distally directed end surface abuts the proximally directed stop surface 59 of the actuator. At this third position, the outwardly directed protrusions 62 of the holding members 60 of the actuator 52 have passed a proximal end surface of the rotator 38, FIG. 9, and have thus moved out of contact with inner surfaces of the rotator 38. The holding members 60 of the actuator 52 are now free to flex outwardly, whereby the inwardly directed protrusions 64 of the holding members 60 are moved out of contact with the recesses 66 of the plunger rod 68.

The flexing of the holding members 60 is rapid and outer surfaces of the holding members 60 will hit the rotator 38, causing an audible and tactile signal that the dose delivery sequence has started. The plunger rod 68 is now free to move in the proximal direction due to the force of the drive spring 72, wherein the proximal end of the plunger rod 68 acts on, and moves, the stopper 20 inside the medicament container 18 in the proximal direction such that a dose of medicament is expelled through the medicament delivery member 24.

When the stopper 20 has been moved by the plunger rod 68 to almost the proximal end inside the medicament container 18, the plunger rod 68 is moved out of contact with the arms 80 of the signalling element 76. The arms 80 of the signalling element 76 are thus free to flex inwards such that the ledges 82 are moved out of contact with the surfaces 84 of the actuator 52, and due to the force of the drive spring 72 in contact with and acting on the base 78 of the signalling element 76, the signalling element 76 will be moved suddenly in the distal direction the distance D until the distal end of the signalling element 76 hits a proximally directed end wall of the actuator, thus providing an audible and tactile signal that the dose delivery sequence is completed and that it is safe to remove the medicament delivery device. It may now be discarded in a safe manner.

It is to be understood that the embodiments described above and shown in the drawings are to be regarded only as non-limiting examples of the invention and that it may be modified in many ways within the scope of the patent claims.

The invention claimed is:

1. A drive mechanism for use with a medicament delivery device, comprising
   - a plunger rod comprising a hollow plunger rod defining a cavity,
   - a drive spring positioned inside the cavity and operably engaged with the plunger rod,
   - an actuator comprising a holding member releasably engaged to the plunger rod for holding said plunger rod with said drive spring in a tensioned state,
   - a rotator operably connected and movable relative to said actuator and configured to interact with said holding member for holding said holding member in engagement with the plunger rod,
   - an activator operably connected to said rotator such that axial movement of the activator in a distal direction relative to the rotator and the actuator causes the rotator to first rotate relative to the actuator and then subsequently to move distally and axially relative to the actuator, wherein the rotation and the axial movement of the rotator relative to the actuator causes the actuator to release the holding member from the plunger rod.

2. The drive mechanism according to claim 1, wherein said actuator is arranged with a guide surface on which said rotator rests when rotated.

3. The drive mechanism according to claim 2, wherein said rotator is arranged with a cut-out in which said guide surface can enter for allowing the axial movement of the rotator in relation to the actuator.

4. The drive mechanism according to claim 1, wherein said rotator comprises first guide ridges that are inclined in relation to a longitudinal direction, wherein said activator acts on the first guide ridges for rotating said rotator.

5. The drive mechanism according to claim 4, wherein said rotator comprises second guide ridges interconnected to said first guide ridges.

6. The drive mechanism according to claim 5, wherein the second guide ridges are generally transversal in relation to the longitudinal direction, wherein said activator acts on the second guide ridges for moving said rotator.

7. The drive mechanism according to claim 1, wherein said rotator comprises first orientating elements operably arranged to interact with second orientating elements on said actuator for providing orientation aid when said rotator is assembled with said actuator.

8. The drive mechanism according to claim 7, wherein said first orientating elements comprise longitudinal grooves.

9. The drive mechanism according to claim 8, wherein said second orientating elements comprise protrusions arranged to fit into said longitudinal grooves.

10. The drive mechanism according to claim 1, further comprising a stop recess on the plunger rod, wherein an inwardly directed protrusion on the actuator fits into the stop recess when said rotator is attached to said actuator.

11. The drive mechanism according to claim 1, wherein said activator is a medicament delivery member guard.

12. The drive mechanism according to claim 1, wherein the rotator comprises at least one guide ridge that is suitable for cooperating with a protrusion of the activator.

13. The drive mechanism according to claim 1, wherein the activator is rotationally fixed relative to the actuator.

14. The drive mechanism according to claim 13, wherein the activator is arranged slidable in relation to the rotator.

15. The drive mechanism according to claim 14, further comprising a guard spring engaged with a distally directed circumferential wall part of the activator biasing the activator proximally.

16. The drive mechanism according to claim 1, wherein the activator comprises a proximal tubular part and first and second distally directed arms extending from the tubular part.

17. A medicament delivery device comprising a drive mechanism according to claim 1.

* * * * *